US012673023B2

(12) United States Patent
Jung et al.

(10) Patent No.: US 12,673,023 B2
(45) Date of Patent: Jul. 7, 2026

(54) MEDICINE CONTAINER COMPRISING LIQUID PHARMACEUTICAL COMPOSITION OF 1-(5-(2,4-DIFLUOROPHENYL)-1-((3-FLUOROPHENYL)SULFONYL)-4-METHOXY-1H-PYRROL-3-YL)-N-METHYLMETHANAMINE

(71) Applicant: Daewoong Pharmaceutical Co., Ltd., Gyeonggi-do (KR)

(72) Inventors: Yeon Jin Jung, Gyeonggi-do (KR); Eun Ji Hong, Gyeonggi-do (KR); Gyoung Won Kim, Gyeonggi-do (KR); Ha Na Hwang, Gyeonggi-do (KR); Gwan Young Kim, Gyeonggi-do (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 259 days.

(21) Appl. No.: 18/560,955

(22) PCT Filed: May 26, 2022

(86) PCT No.: PCT/KR2022/007489
§ 371 (c)(1),
(2) Date: Nov. 15, 2023

(87) PCT Pub. No.: WO2022/250472
PCT Pub. Date: Dec. 1, 2022

(65) Prior Publication Data

US 2024/0269070 A1 Aug. 15, 2024

(30) Foreign Application Priority Data

May 26, 2021 (KR) .................. KR10-2021-0067635
May 26, 2022 (KR) .................. KR10-2022-0064452

(51) Int. Cl.
*A61K 9/08* (2006.01)
*A61J 1/05* (2006.01)
*A61J 1/14* (2023.01)
*A61K 31/4015* (2006.01)
*A61K 47/26* (2006.01)
*A61K 47/40* (2006.01)

(52) U.S. Cl.
CPC *A61K 9/08* (2013.01); *A61J 1/05* (2013.01); *A61J 1/1468* (2015.05); *A61K 31/4015* (2013.01); *A61K 47/26* (2013.01); *A61K 47/40* (2013.01)

(58) Field of Classification Search
CPC ...... A61K 9/08; A61K 31/4015; A61K 47/26; A61K 47/40; A61K 9/0019; A61K 9/19; A61J 1/05; A61J 1/1468; A61J 1/06; A61P 1/04
See application file for complete search history.

(56) References Cited

U.S. PATENT DOCUMENTS

| | | | |
|---|---|---|---|
| 8,053,599 | B2 | 11/2011 | Sudoh et al. |
| 10,023,495 | B2 | 7/2018 | Chang et al. |
| 10,100,010 | B1 | 10/2018 | Lee et al. |
| 10,273,048 | B2 | 4/2019 | Fadeev et al. |
| 2015/0098084 | A1 | 4/2015 | Felts et al. |
| 2015/0297800 | A1 | 10/2015 | Weikart et al. |
| 2015/0299851 | A1 | 10/2015 | Bicker et al. |
| 2016/0251261 | A1 | 9/2016 | Bureau |
| 2024/0261261 | A1 | 8/2024 | Jung et al. |

FOREIGN PATENT DOCUMENTS

| | | | |
|---|---|---|---|
| CL | 201702571 | A1 | 3/2018 |
| CL | 202303477 | A1 | 5/2024 |
| CN | 202753490 | U | 2/2013 |
| EP | 3197867 | B1 | 11/2018 |
| EP | 3854784 | A1 | 7/2021 |
| JP | H06-76233 | B2 | 9/1994 |
| JP | H07-179359 | A | 7/1995 |
| JP | H10-114374 | A | 5/1998 |
| JP | 2000-219621 | A | 8/2000 |
| JP | 2003-267872 | A | 9/2003 |
| JP | 2010-243091 | A | 10/2010 |
| JP | 2017-515513 | A | 6/2017 |
| JP | 2019-509320 | A | 4/2019 |
| JP | 2019089691 | A | 6/2019 |
| KR | 101144553 | B1 | 5/2012 |
| KR | 101613245 | B1 | 4/2016 |
| KR | 101818704 | B1 | 2/2018 |
| KR | 101829705 | B1 | 2/2018 |
| KZ | 33472 | B | 2/2019 |
| RU | 2634758 | C2 | 11/2017 |
| RU | 2663895 | C1 | 8/2018 |
| RU | 2679454 | C2 | 2/2019 |
| TW | 202302085 | A | 1/2023 |
| WO | WO-2010/013823 | A2 | 2/2010 |
| WO | WO-2010/024451 | A1 | 3/2010 |
| WO | WO-2011/121811 | A1 | 10/2011 |
| WO | WO-2011/125241 | A1 | 10/2011 |

(Continued)

OTHER PUBLICATIONS

Miyamoto (JP2019089691A Machine Translation) (Year: 2019).*
Sugiyama et al., "Deposition of Shield-Film to Pharmaceutical Glass Vessels (2)", Reports of the Fuji Industrial Research Institute of Shizuoka Prefecture, No. 14, Dec. 2004, 8 pages.
Office Action in JP Application No. 2023-571145 dated Jan. 14, 2025, 11 pages.
Office Action in TW Application No. 112142889 dated Mar. 11, 2015, 4 pages.

(Continued)

*Primary Examiner* — Quanglong N Truong
(74) *Attorney, Agent, or Firm* — MARSHALL, GERSTEIN & BORUN LLP

(57) ABSTRACT

The present disclosure relates to a medicine container containing a liquid pharmaceutical composition of 1-(5-(2,4-difluorophenyl)-1-((3-fluorophenyl)sulfonyl)-4-methoxy-1H-pyrrol-3-yl)-N-methylmethanamine, or a pharmaceutically acceptable salt thereof.

6 Claims, No Drawings

(56) References Cited

FOREIGN PATENT DOCUMENTS

| | | | | | |
|---|---|---|---|---|---|
| WO | WO-2016175555 | A2 * | 11/2016 | ................ | A61P 1/16 |
| WO | WO-2017/164575 | A1 | 9/2017 | | |
| WO | WO-2017/164576 | A1 | 9/2017 | | |
| WO | WO-2018/221971 | A1 | 12/2018 | | |
| WO | WO-2018/236153 | A1 | 12/2018 | | |

OTHER PUBLICATIONS

Office Action in AU Application No. 2022280595 dated Aug. 9, 2024, 5 pages.
Search Report in International Application No. PCT/KR2022/007489 filed Sep. 6, 2022, 8 pages.
Office Action in RU Application No. 2023128224/04(062851) dated Jun. 5, 2024, 17 pages.
Notice of Opposition in Ecuador Application No. 2023-89215 dated Jul. 2, 2024, 113 pages.
Supplementary European Search Report in EP Application No. 22811663.8 dated Jun. 2, 2025, 11 pages.
Loftsson et al., “Pharmaceutical Applications of Cyclodextrins. 1. Drug Solubilization and Stabilization”, Journal of Pharmaceutical Sciences, vol. 85, No. 10, Oct. 1, 1996, pp. 1017-1025.
European Pharmacopoeia: “European 7.0 Section 3.2.1 Glass Containers for Pharmaceutical Use”, Jan. 1, 2008, 5 pages.
Database Medline, Loftsson Thorsteinn, “Cyclodextrins in Parenteral Formulations”, Feb. 2021, Database accession No. NLM33069709, 2 pages.
Office Action in KZ Application No. 2023/0799.1 dated Aug. 4, 2025, 12 pages.
Office Action in CL Application No. 202303478 dated Sep. 22, 2025, 28 pages.

* cited by examiner

MEDICINE CONTAINER COMPRISING LIQUID PHARMACEUTICAL COMPOSITION OF 1-(5-(2,4-DIFLUOROPHENYL)-1-((3-FLUOROPHENYL)SULFONYL)-4-METHOXY-1H-PYRROL-3-YL)-N-METHYLMETHANAMINE

CROSS-REFERENCE TO RELATED APPLICATION(S)

This application claims the benefit of Korean Patent Application No. 10-2021-0067635 filed on May 26, 2021 and Korean Patent Application No. 10-2022-0064452 filed on May 26, 2022 in the Korean Intellectual Property Office, the disclosures of which are incorporated herein by reference in their entirety.

TECHNICAL FIELD

The present disclosure relates to a medicine container comprising a liquid pharmaceutical composition containing 1-(5-(2,4-difluorophenyl)-1-((3-fluorophenyl)sulfonyl)-4-methoxy-1H-pyrrol-3-yl)-N-methylmethanamine.

BACKGROUND ART 1-(5-(2,4-Difluorophenyl)-1-((3-fluorophenyl)sulfonyl)-4-methoxy-1H-pyrrol-3-yl)-N-methylmethanamine is a substance described in Korean Patent Registration No. 10-1613245, which is a substance that has excellent anti-ulcer activity (i.e., proton pump inhibitory activity, etc.), anti-*Helicobacter pylori* (*H. pylori*) activity and GPCR inhibitory activity, and thus is useful for the prevention and treatment of gastrointestinal ulcers, gastritis, reflux esophagitis, or gastrointestinal damage caused by *Helicobacter pylori.*

However, the present inventors confirmed that the composition is decreased in the stability when stored as a liquid formulation during long period of time, and conducted diligent research on the causes of such long-term stability problems. As a result, the inventors confirmed that the material reacts with an acid or base so that decomposition products can be increased, particularly, the acid/base reaction is accelerated in the steps of wet heat sterilization, dry sterilization and the like, which are high-temperature sterilization processes generally required in the production process for liquid formulations, and thus there were difficulties in developing a stable liquid formulation containing Chemical Formula 1 described later.

In this regard, the present inventors has found that when a liquid pharmaceutical composition containing 1-(5-(2,4-difluorophenyl)-1-((3-fluorophenyl)sulfonyl)-4-methoxy-1H-pyrrol-3-yl)-N-methylmethanamine, or a pharmaceutically acceptable salt thereof is stored as a liquid formulation in a standard glass vial for a long period of time, the solution may react with the alkaline substance derived from the inner surface of the vial, making it difficult to ensure stability, which may lead to great difficulties in commercialization. The inventors endeavored to provide a medicine container for ensuring stable storage for a long period of time, and as a result, found that when a container made of a specific material is used, the reaction between the pharmaceutical composition and the container is minimized and so the storage is facilitated, it enables provision of a pharmaceutical product in the form of ready-to-use infusion solution formulation, and has stability even after going through a high temperature sterilization process, thereby completing the present disclosure.

DETAILED DESCRIPTION OF THE INVENTION

Technical Problem

It is an object of the present disclosure to provide a medicine container comprising a liquid pharmaceutical composition containing 1-(5-(2,4-difluorophenyl)-1-((3-fluorophenyl)sulfonyl)-4-methoxy-1H-pyrrol-3-yl)-N-methylmethanamine, or a pharmaceutically acceptable salt thereof.

Technical Solution

According to an embodiment of the present disclosure, there is provided a medicine container comprising: a liquid pharmaceutical composition containing a compound represented by the following Chemical Formula 1 or a pharmaceutically acceptable salt thereof:

[Chemical Formula 1]

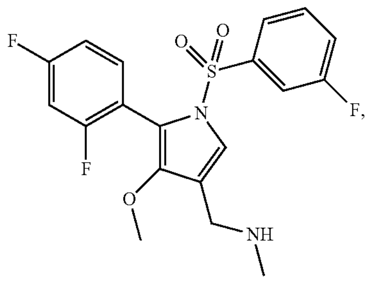

wherein the medicine container includes a plastic container; a glass container whose inside face is coated with silicone oil, $SiO_2$, or SiOCH; or a dealkalized glass container.

The chemical name of the compound represented by Chemical Formula 1 is 1-(5-(2,4-difluorophenyl)-1-((3-fluorophenyl)sulfonyl)-4-methoxy-1H-pyrrol-3-yl)-N-methylmethanamine, which is a substance described in Korean Patent Registration No. 10-1613245.

The compound represented by Chemical Formula 1 is an active ingredient exhibiting the pharmacological effect of the liquid pharmaceutical composition of the present disclosure, which is a substance that has excellent anti-ulcer activity (i.e., proton pump inhibitory activity, etc.), anti-*Helicobacter pylori* (*H. pylori*) activity and GPCR inhibitory action and thus is useful for the prevention and treatment of gastrointestinal ulcers, gastritis, reflux esophagitis, or gastrointestinal damage caused by *Helicobacter pylori.*

In addition, as an active ingredient exhibiting the pharmacological effect of the liquid pharmaceutical composition of the present disclosure, not only the compound represented by Chemical Formula 1 but also a pharmaceutically acceptable salt thereof can be used. As salts, salts commonly used in the art, such as acid addition salts formed by pharmaceutically acceptable free acids can be used without limitation. The term "pharmaceutically acceptable salt" as used herein refers to any organic or inorganic addition salt of the compound represented by Chemical Formula 1, whose concentration is relatively non-toxic and harmless to ae patient and activates effectively and whose side effects do not degrade the beneficial efficacy of the above compound.

Pharmaceutically acceptable salts can be obtained by conventional methods using inorganic or organic acids. For example, the pharmaceutically acceptable salt can be prepared by dissolving the compound represented by Chemical Formula 1 in a water-miscible organic solvent, e.g., acetone, methanol, ethanol or acetonitrile, followed by adding an organic acid or an inorganic acid, and filtering and drying the precipitated crystals. Alternatively, it can be prepared by subjecting a solvent or an excessive amount of acid from the acid-added reaction mixture to reduced pressure and then drying the residue, or by adding a different organic solvent and then filtering the precipitated salt. At this time, the preferred salts may include salts derived from hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid or toluenesulfonic acid, and the like.

Meanwhile, the compound represented by Chemical Formula 1 or a pharmaceutically acceptable salt thereof reacts with an acid or a base so that decomposition products can be increased. Therefore, when the liquid pharmaceutical composition thereof is stored in a standard container for a long period of time, the solution may react with an alkaline substance derived from the inner surface of the container. In particular, when a general standard glass container is used, there is a problem that the above reaction is performed more actively. Therefore, in order to more easily store the liquid formulation for a long period of time, a medicine container containing the liquid pharmaceutical composition is a plastic container instead of a glass, or a glass container functionally coated with a specific material, or a dealkalized container is used. If a plastic container is used, the plastic container is not particularly limited, but may preferably be a Cyclic Olefin Polymer (COP) or a Cyclic Olefin Copolymer (COC). More preferably, it may be a cyclic olefin polymer. Further, as the inner coating material of the glass container, silicone oil, $SiO_2$, or SiOCH having low reactivity with the liquid formulation can be used, and a dealkalized glass container in which an alkali material is removed from the surface inside the container by acid treatment inside the general glass container can be used. By coating or processing with a specific material in this way, or using a container made of a specific material, the liquid pharmaceutical composition is increased in stability, can be commercialized and can also be usefully used as a ready-to-use infusion solution formulation.

In addition, acid/base reaction can be accelerated in steps such as wet heat sterilization and dry sterilization, which are high-temperature sterilization processes generally required in liquid preparations, but when a particular container is used, the stability of the compound can be maintained even at these steps.

Meanwhile, the liquid pharmaceutical composition may further include cyclodextrin and an isotonizing agent.

The compound represented by Chemical Formula 1 or a pharmaceutically acceptable salt thereof has low water solubility, so an excessive amount of a solubilizing agent and an organic solvent are required in order to prepare into a liquid pharmaceutical composition, such as a pharmaceutical composition for injection. However, an excessive amount of solubilizers and the like may cause hypersensitivity when administered to a patient. Therefore, in the present invention, the above-mentioned ingredients is used instead of using the solubilizer generally used in a liquid pharmaceutical composition, thereby obtaining a liquid pharmaceutical composition having both excellent solubility and stability of the compound represented by Chemical Formula 1.

The cyclodextrin is a cyclic oligosaccharide in which 6 to 12 glucose molecules are alpha-1,4-glycosidic bonds, and is used as a stabilizer in the present disclosure. Preferably, the cyclodextrin is beta-cyclodextrin, or gamma-cyclodextrin, more preferably, beta-cyclodextrin. More preferably, the beta-cyclodextrin is (2-hydroxypropyl)-beta-cyclodextrin or sulfobutylether-beta-cyclodextrin, whose English abbreviations are 'HP-β-CD' and 'SBE-β-CD', respectively. Most preferably, preferably, the beta-cyclodextrin is (2-hydroxypropyl)-beta-cyclodextrin (HP-β-CD).

Among the stabilizers commonly used in liquid pharmaceutical compositions, the cyclodextrin is suitable for stabilizing the compound represented by Chemical Formula 1 or a pharmaceutically acceptable salt thereof.

Preferably, the cyclodextrin is used in an amount of 3.0 to 25.0 parts by weight with respect to 1 part by weight of the compound represented by Chemical Formula 1 or a pharmaceutically acceptable salt thereof. When the content is less than 3.0 parts by weight, it is not sufficient to stabilize the compound represented by Chemical Formula 1, which may cause a problem that rehydration of the liquid pharmaceutical composition is difficult or the total related substances increases during long-term storage. Further, when the content is greater than 25.0 parts by weight, the amount of the stabilizer used is too larger and thus, the viscosity of the liquid pharmaceutical composition become high, or there is a risk of causing hypersensitivity when administered to a patient.

More preferably, the content of the cyclodextrin is 3.5 parts by weight or more, 4.0 parts by weight or more, or 4.5 parts by weight or more; and 20.0 parts by weight or less, 19.0 parts by weight or less, 18.0 parts by weight or less, 17.0 parts by weight or less, 16.0 parts by weight or less, 15.0 parts by weight or less, 14.0 parts by weight or less, 13.0 parts by weight or less, 12.0 parts by weight or less, 11.0 parts by weight or less; or 10.0 parts by weight or less, with respect to 1 part by weight of the compound represented by Chemical Formula 1 or a pharmaceutically acceptable salt thereof.

Meanwhile, the 'isotonic agent' is an additive added to make the osmotic pressure of the liquid pharmaceutical composition contained in the container similar to the osmotic pressure in the body. Since the liquid pharmaceutical composition is administered directly into the body without a separate dilution process, it should be manufactured at the same osmotic pressure as the body in order to reduce side effects when administered in the body. Preferably, the isotonizing agent may be sodium chloride (NaCl), D-mannitol, dextrose, glycerin, or KCl (potassium chloride), more preferably, sodium chloride (NaCl), dextrose, glycerin, or KCl (potassium chloride), and most preferably, sodium chloride (NaCl), dextrose, or KCl (potassium chloride).

The isotonizing agent may differ in the content required to reach the osmolarity of the desired liquid pharmaceutical composition, depending on whether it is an electrolyte or a non-electrolyte. Therefore, the isotonizing agent is preferably contained so that the osmolality of the liquid pharmaceutical composition according to the present disclosure may be 100 to 700 mOsmol/L depending on the type of specific substance. More preferably, the osmolality of the formulation for injection may be 150 to 650 mOsmol/L, 150 to 450 mOsmol/L, 250 to 450 mOsmol/L, or 270 to 420 mOsmol/L.

Preferably, the liquid pharmaceutical composition may further include a freeze-drying aid. Generally, the liquid pharmaceutical compositions are mass-produced, then frozen, and stored and distributed under reduced pressure, which can enhance the stability of the active ingredient and improve the long-term storage stability. Therefore, the stability of the active substance must be maintained during the process of freeze-drying, and thus, in the present disclosure, a freeze-drying aid can be further included. Preferably, the freeze-drying aid may be D-mannitol, sucrose, sorbitol, or trihalose, and more preferably, the freeze-drying aid may be D-mannitol.

Preferably, the freeze-drying aid is used in an amount of 3.0 to 25.0 parts by weight with respect to 1 part by weight of the compound represented by Chemical Formula 1 or a pharmaceutically acceptable salt thereof. When the content is less than 3.0 parts by weight, it is not sufficient for stabilizing the compound represented by Chemical Formula 1, which may cause a problem that rehydration of the liquid pharmaceutical composition is difficult or the related substances increase during long-term storage. Further, when the content is greater than 25.0 parts by weight, the amount of the freeze-drying aid is too large, and thus, the viscosity of the liquid pharmaceutical composition become high, or there is a risk of causing hypersensitivity when administered to a patient.

More preferably, the content of the freeze-drying aid is 3.5 parts by weight or more, 4.0 parts by weight or more, or 4.5 parts by weight or more; and 20.0 parts by weight or less, 15.0 parts by weight or less, 13.0 parts by weight or less, 10.0 parts by weight or less, 9.0 parts by weight or less, 8.0 parts by weight or less, 7.0 parts by weight or less, or 6.0 parts by weight or less with respect to 1 part by weight of the compound represented by Chemical Formula 1 or a pharmaceutically acceptable salt thereof.

Preferably, the freeze-drying aid is used in an amount of 0.5 to 5.0 parts by weight with respect to 1 part by weight of the cyclodextrin. More preferably, the content of the freeze-drying aid is 0.6 parts by weight or more, 0.7 parts by weight or more, or 0.8 or more; and 4.5 parts by weight or less, 4.0 parts by weight or less, 3.5 parts by weight or less, 3.0 parts by weight or less, 2.5 parts by weight or less, 2.3 parts by weight or less, 2.0 parts by weight or less, 1.9 parts by weight or less, 1.8 parts by weight or less, 1.7 parts by weight or less; 1.6 parts by weight or less, 1.5 parts by weight or less, 1.4 parts by weight or less, 1.3 parts by weight or less, or 1.2 parts by weight or less with respect to 1 part by weight of the cyclodextrin.

Preferably, in order to prepare the pharmaceutical composition in liquid form, a solvent commonly used in the art can be used. As an example, the solvent of the liquid pharmaceutical composition is distilled water, water for injection, acetate buffer, or physiological saline.

Preferably, the pH of the liquid pharmaceutical composition according to the present invention is 4.0 to 6.0, more preferably 5.0 to 6.0. Due to the chemical properties of the liquid pharmaceutical composition of the present disclosure, an additional pH adjusting agent may not be used for adjusting the pH. Here, the pH adjusting agent is a substance that adjusts the pH of the solution by adding the agent to thereby improve the solubility of poorly water-soluble or insoluble compounds, and a pharmaceutically acceptable acid or alkali agent is used. Examples thereof may include any one or more of hydrochloric acid, phosphoric acid, sodium hydroxide, potassium hydroxide, potassium monohydrogen phosphate, potassium dihydrogen phosphate, sodium monohydrogen phosphate, sodium dihydrogen phosphate, sodium carbonate, potassium carbonate and triethanolamine.

Preferably, the compound represented by Chemical Formula 1 or a pharmaceutically acceptable salt thereof is contained in an amount of 1 to 8 mg/mL in the liquid pharmaceutical composition. That is, the content of the compound represented by Chemical Formula 1 or a pharmaceutically acceptable salt thereof can be defined as a value obtained by dividing the content (mg) of the compound represented by Chemical Formula 1 or a pharmaceutically acceptable salt thereof by the total volume (mL) of the liquid pharmaceutical composition.

More preferably, the compound represented by Chemical Formula 1 or a pharmaceutically acceptable salt thereof is contained in an amount of 2 mg/ml or more, 3 mg/ml or more, or 4 mg/mL or more, or 5 mg/ml or more; and 7 mg/mL or less, 6 mg/ml or less, or 5.5 mg/mL or less in the liquid pharmaceutical composition.

Meanwhile, the 'amount of related substances', which will be described later, is analyzed by the related substance test method set in accordance with the ICH Guideline Q2 Analytical Validation. The total amount of related substances is calculated through the proportional formula between the concentration of the known purity standard, the peak area measured by HPLC, the concentration of the test solution, and the peak area of the related substance measured by HPLC. Specifically, 'Amount (%) of related substances' can be calculated by '(Standard solution concentration (mg/mL)/Test solution concentration (mg/mL))*(Peak area of related substances in sample solution/Peak area of standard solution)*100'.

When the medicine container is stored under harsh conditions of 60° C. and 80% RH for 4 weeks, the amount of related substances generated in the liquid pharmaceutical composition may be 0.5% or less. Preferably, the amount of related substances in the liquid pharmaceutical composition in the medicine container stored under the harsh conditions for 4 weeks may be 0.48% or less, 0.47% or less, 0.46% or less, or 0.45% or less.

Further, the difference between the amount of related substances in the liquid pharmaceutical composition measured after storing the medicine container under severe conditions of 60° C. and 80% RH for 4 weeks and the amount of related substances before being treated under harsh conditions may be 0.45% or less. Preferably, the difference between the amount of related substances in the liquid pharmaceutical composition measured after being stored for 4 weeks and the amount of related substances before being treated under harsh conditions may be 0.43% or less, 0.4% or less, 0.38% or less, 0.36% or less, or 0.35% or less.

Preferably, the amount of related substances in the liquid pharmaceutical composition measured after heat-sterilizing the medicine container at 100° ° C. to 150° C. for 3 to 30 minutes and storing it under severe conditions of 60° C. and 80% RH for 4 weeks may be 0.5% or less. Preferably, the amount of related substances in the liquid pharmaceutical composition in the medicine container stored under severe conditions for 4 weeks after the heat sterilization treatment may be 0.48% or less, 0.47% or less, 0.46% or less, or 0.45% or less. More preferably, the heat sterilization treatment conditions may be 15 minutes at 121° C., 10 minutes at 126° C., or 3 minutes at 134° C.

Preferably, the difference between the amount of related substances in the liquid pharmaceutical composition measured after heat-sterilizing the medicine container at 100° ° C. to 150° C. for 3 to 30 minutes and storing it under severe conditions of 60° C. and 80% RH for 4 weeks and the amount of related substances before being treated under harsh conditions is 0.45% or less. Preferably, the difference between the amount of related substances in the liquid pharmaceutical composition measured after being stored for 4 weeks after the heat sterilization treatment and the amount of related substances before being treated under harsh conditions may be 0.43% or less, 0.4% or less, 0.38% or less, 0.36% or less, or 0.35% or less. More preferably, the heat sterilization treatment conditions may be 15 minutes at 121° C., 10 minutes at 126° C., or 3 minutes at 134° C.

If necessary, the liquid pharmaceutical composition according to the present disclosure may further include a preservative, an antioxidant, and the like. The preservative and the antioxidant are not particularly limited as long as they are commonly used in the technical field to which the present disclosure pertains.

In addition, the liquid pharmaceutical composition according to the present disclosure can be prepared by mixing the above-mentioned ingredients excluding the solvent with a solvent. In this process, the order of addition to the solvent of each component can be adjusted as needed, or all components can be mixed and added to the solvent before being added to the solvent.

Advantageous Effects

As described above, the medicine container of the present disclosure can stably store a liquid pharmaceutical composition containing 1-(5-(2,4-difluorophenyl)-1-((3-fluorophenyl) sulfonyl)-4-methoxy-1H-pyrrol-3-yl)-N-methylmethanamine, or a pharmaceutically acceptable salt thereof, and thus the medicine container containing the liquid pharmaceutical composition can be usefully used as a ready-to-use infusion solution formulation.

DETAILED DESCRIPTION OF THE EMBODIMENTS

Hereinafter, preferred examples are presented in order to help easy understanding of the present disclosure, but the following examples are for illustrative purposes only and the scope of the present disclosure is not limited thereby.

Example 1

As shown in Table 1 below, a liquid pharmaceutical composition containing a hydrochloride salt of the compound represented by Chemical Formula 1 (hereinafter referred to as 'API') was prepared.

TABLE 1

| | #1-1 | #1-2 |
|---|---|---|
| API | 40 mg | |
| HP-β-CD | 200 mg | |
| D-mannitol | 200 mg | |
| NaCl | 90 mg | |
| water for injection | 10 mL | |
| pH (HCl/NaOH) | added 6.0 | not added 5.0 |

Each prepared solution is filled into vials made of different materials as shown in Table 2 below, and stored in liquid form under harsh conditions (60° C., 80% RH) chamber for 4 weeks, and then the stability was evaluated and shown in Table 3 below. For the stability evaluation, the amount of a related substance of a liquid solution was analyzed by HPLC, and the total amount of the detected related substance was measured.

Specifically, the amount of related substances was analyzed by the related substance test method set in accordance with the ICH Guideline Q2 Analytical Validation. The total amount of related substances was calculated through the proportional formula of the concentration of the known purity standard, the peak area measured by HPLC, the concentration of the test solution, and the peak area of the related substance measured by HPLC.

The plastic vials used in #2-9 and #2-10 in Table 2 below are Daikyo Crystal Zenith vials.

TABLE 2

| | #2-1 | #2-2 | #2-3 | #2-4 | #2-5 | #2-6 | #2-7 | #2-8 | #2-9 | #2-10 |
|---|---|---|---|---|---|---|---|---|---|---|
| API | 40 mg | | | | | | | | | |
| HP-β-CD | 200 mg | | | | | | | | | |
| D-mannitol | 200 mg | | | | | | | | | |
| NaCl | 90 mg | | | | | | | | | |
| Water for injection | 10 mL | | | | | | | | | |
| Vial | General glass vial | | Silicone oil-coated glass vial | | $SiO_2$ -coated glass vial | | SiOCH-coated glass vial | | Plastic vial | |
| pH (HCl/NaOH) | added 6.0 | not added 5.0 | added 6.0 | not added 5.0 | added 6.0 | not added 5.0 | added 6.0 | not added 5.0 | added 6.0 | not added 5.0 |

TABLE 3

| | Properties | | Total related substance % | |
|---|---|---|---|---|
| | Before treatment | After 4 weeks | Before treatment | After 4 weeks |
| #2-1 | colorless transparent liquid | colorless transparent liquid | 0.03 | 0.63 |
| #2-2 | colorless transparent liquid | colorless transparent liquid | 0.05 | 0.51 |
| #2-3 | colorless transparent liquid | colorless transparent liquid | 0.04 | 0.33 |
| #2-4 | colorless transparent liquid | colorless transparent liquid | 0.04 | 0.33 |
| #2-5 | colorless transparent liquid | colorless transparent liquid | 0.04 | 0.19 |
| #2-6 | colorless transparent liquid | colorless transparent liquid | 0.02 | 0.26 |
| #2-7 | colorless transparent liquid | colorless transparent liquid | 0.04 | 0.17 |
| #2-8 | colorless transparent liquid | colorless transparent liquid | 0.04 | 0.12 |

TABLE 3-continued

| | Properties | | Total related substance % | |
|---|---|---|---|---|
| | Before treatment | After 4 weeks | Before treatment | After 4 weeks |
| #2-9 | colorless transparent liquid | colorless transparent liquid | 0.03 | 0.13 |
| #2-10 | colorless transparent liquid | colorless transparent liquid | 0.04 | 0.28 |

As shown in Table 3 above, it can be confirmed that when stored in a liquid solution state under harsh conditions for each container for 4 weeks, there were no changes in the properties, but in the functional container of an embodiment of the present disclosure, the total related material production degree is relatively lower than Comparative Examples #2-1 and #2-2 using a general glass vial. That is, it was confirmed that it has stability when the liquid solution was stored in the medicine container of an embodiment of the present disclosure.

Example 2

For compositions to which moist heat sterilization (sterilized at 121° C. for 15 minutes) was applied, which is necessary during the liquid formulation production process but can accelerate the reactivity with acids/bases, an attempt was made to confirm whether there was a similar long-term stability improvement effect.

A liquid composition was prepared in the same manner as in Example 1, and the stability was evaluated in the same manner as in Example 1.

Acid-treated glass vials are dealkalized vials in which alkali materials are removed by acid-treating the inner surface of general glass vials.

TABLE 4

| | #2-2 | #3-1 | #3-2 | #3-3 | #2-4 | #3-4 |
|---|---|---|---|---|---|---|
| API | 40 mg | | | | | |
| HP-β-CD | 200 mg | | | | | |
| D-mannitol | 200 mg | | | | | |
| NaCl | 90 mg | | | | | |
| Water for injection | 10 mL | | | | | |
| pH (HCl/NaOH) | Not added | | | | | |
| Vial | General glass vial | | Acid-treated glass vial (dealkalized) | | Silicone oil-coated glass vial | |
| wet heat sterilization (121° C., 15 min) | Not applied | Applied | Not applied | Applied | Not applied | Applied |

TABLE 5

| | Properties | | Total related substance % | |
|---|---|---|---|---|
| | Before treatment | After 4 weeks | Before treatment | After 4 weeks |
| #2-2 | colorless transparent liquid | colorless transparent liquid | 0.05 | 0.51 |
| #3-1 | colorless transparent liquid | colorless transparent liquid | 0.20 | 0.88 |
| #3-2 | colorless transparent liquid | colorless transparent liquid | 0.06 | 0.29 |
| #3-3 | colorless transparent liquid | colorless transparent liquid | 0.10 | 0.45 |
| #2-4 | colorless transparent liquid | colorless transparent liquid | 0.04 | 0.33 |

TABLE 5-continued

| | Properties | | Total related substance % | |
|---|---|---|---|---|
| | Before treatment | After 4 weeks | Before treatment | After 4 weeks |
| #3-4 | colorless transparent liquid | colorless transparent liquid | 0.08 | 0.41 |

As shown in Table 5, it can be confirmed that when wet heat sterilization was not applied, there are no changes in the properties when stored in a liquid solution state under harsh conditions for each container for 4 weeks, but in the functional containers (#3-2 and #2-4) of an embodiment of the present disclosure, the total related material production degree is relatively lower than Comparative Examples #2-1 using a general glass vial. In particular, it was confirmed that it has more stability in a dealkalized container.

It can be confirmed that when the wet heat sterilization step, which is generally required for liquid formulations, is applied, there are more related substances before being treated under harsh conditions than when wet heat sterilization is not applied, from which it can be inferred that the acid/base reactivity increased during the wet heat sterilization process. In addition, it can be confirmed that when wet heat sterilization is applied, the increase of related substances after 4 weeks in each vial is higher than when not applied, from which it is presumed that the alkali activation of the inner surface of the vial is increased due to the high temperature during wet heat sterilization. Nevertheless, in acid-treated vials and inner-coated vials, the effect of such heat sterilization step was minimized, showing superior stability maintenance effect as compared to general vials, thereby presenting the possibility of commercialization of liquid formulations including Chemical Formula 1.

From the above Examples, it was confirmed that it has stability when storing the liquid solution in the medicine container of one embodiment of the present disclosure.

The invention claimed is:

1. A medicine container comprising a liquid pharmaceutical composition containing a compound represented by the following Chemical Formula 1 or a pharmaceutically acceptable salt thereof:

[Chemical Formula 1]

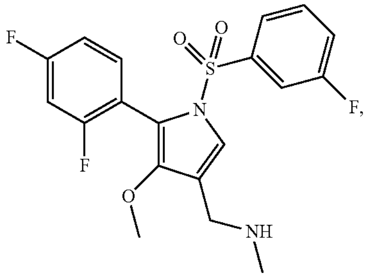

wherein the liquid pharmaceutical composition further comprises an isotonizing agent, wherein the isotonizing agent is D-mannitol or NaCl, wherein the liquid pharmaceutical composition comprises a beta-cyclodextrin in an amount of 3.0 parts by weight to 25 parts by weight with respect to one part by weight of said compound of Chemical Formula 1, wherein the medicine container comprises a cyclic olefin polymer (COP) or cyclic olefin copolymer (COC) plastic container; a glass container whose inside face is coated with silicone oil, $SiO_2$, or SiOCH; or a dealkalized glass container, and wherein an amount of related substances in the liquid pharmaceutical composition measured after storing the medicine container under harsh conditions of 60° C. and 80% RH for 4 weeks is 0.5% or less.

2. The medicine container of claim 1, wherein the beta-cyclodextrin is (2-hydroxypropyl)-beta-cyclodextrin.

3. The medicine container of claim 1, wherein the liquid pharmaceutical composition has a pH of 4.0 to 6.0.

4. The medicine container of claim 1, wherein a difference between the amount of related substances in the liquid pharmaceutical composition measured after storing the medicine container under said harsh conditions of 60° C. and 80% RH for 4 weeks and an amount of related substances before being stored under said harsh conditions is 0.45% or less.

5. The medicine container of claim 1, wherein an amount of related substances in the liquid pharmaceutical composition measured after heat-sterilizing the medicine container at 100° C. to 150° C. for 3 minutes to 30 minutes and storing it under said harsh conditions of 60° C. and 80% RH for 4 weeks is 0.5% or less.

6. The medicine container of claim 1, wherein a difference between an amount of related substances in the liquid pharmaceutical composition measured after heat-sterilizing the medicine container at 100° C. to 150° C. for 3 minutes to 30 minutes, and storing it under said harsh conditions of 60° C. and 80% RH for 4 weeks and the amount of related substances before being treated under said harsh conditions is 0.45% or less.

* * * * *